United States Patent [19]

Meyer

[11] Patent Number: 5,166,445

[45] Date of Patent: Nov. 24, 1992

[54] METHOD FOR THE MANUFACTURE OF CAROTINOIDS AND THE NOVEL INTERMEDIATES

[75] Inventor: Karl Meyer, Liestal, Switzerland

[73] Assignee: Hoffman-La Roche Inc., Nutley, N.J.

[21] Appl. No.: 463,698

[22] Filed: Jan. 11, 1990

[30] Foreign Application Priority Data

Feb. 10, 1989 [CH] Switzerland ................ 468/89

[51] Int. Cl.$^5$ ............................................. C07F 5/02
[52] U.S. Cl. ........................... 568/2; 562/606; 562/607; 568/9
[58] Field of Search .......... 562/606, 607; 568/9, 568/2; 558/286

[56] References Cited

U.S. PATENT DOCUMENTS 3,755,457 8/1973 Carlson ........................ 562/607
4,182,731 1/1980 Schulz et al. ................... 568/9

OTHER PUBLICATIONS

Manchand et al, *J. Chem. Soc.*, 2019-26 (1965).
Eidem et al., Acta Chemica Scandinavica B., 29, 1015-23 (1975).
Marki-Fischer et al., Helvetica Chimica Acta, 66 (Mar. 1983).
Chem. Abstracts. vol. 81 49884c. (1974).
Chem. Abstracts, vol. 84 44452n (1976).

*Primary Examiner*—Jose G. Dees
*Assistant Examiner*—B. Frazier
*Attorney, Agent, or Firm*—George M. Gould; William H. Epstein; Bruce A. Pokras

[57] ABSTRACT

Phosphonium salts of the formula

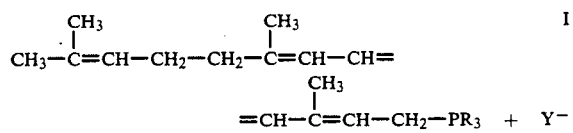

wherein A signifies aryl and $Y^-$ signifies $C_1$-$C_6$-alkanoate or hydroxytrifluoroborate, as well as their manufacture from 3,7,11-trimethyldodeca-1,4,6,10-tetraen-3-ol with a triarylphosphine and with a $C_1$-$C_6$-alkanoic acid or a boron trifluoride etherate and, if desired after conversion into the phosphonium salt of a strong acid, further reaction to give lycopene.

1 Claim, No Drawings

METHOD FOR THE MANUFACTURE OF CAROTINOIDS AND THE NOVEL INTERMEDIATES

BACKGROUND OF THE INVENTION

The present invention is concerned with the manufacture of 3,7,11-trimethyldodeca-2,4,6,10-tetraen-1-yl-phosphonium salts and of lycopene and with novel 3,7,11-trimethyldodeca-2,4,6,10-tetraen-1-yl-phosphonium salts in this process.

Lycopene is a natural red carotinoid which occurs e.g. in tomatoes.

Carotinoids are manufactured mainly by a Wittig reaction from phosphonium salts and aldehydes. The phosphonium salts which are used are salts of strong acids-usually halides, sulphates or phosphates-and are obtained as a rule from the corresponding alcohols, halides etc. However, the manufacture of lycopene according to this method gives only low yields, with especially in the production of the phosphonium salts predominantly unreactive byproducts being formed.

It has now been found that 3,7,11-trimethyldodeca-2,4,6,10-tetraen-1-yl-phosphonium alkanoates and -phosphonium hydroxytrifluoroborates can be manufactured in high yield and that these can be reacted further in a Wittig reaction just as the usual phosphonium salts of strong acids. If desired, the alkanoates and hydroxytrifluoroborates can be converted, prior to the conversion into lycopene, in a simple manner into the phosphonium salts of usual strong acids, whereby the latter can be obtained via the alkanoates and hydroxytrifluoroborates in substantially higher yield.

SUMMARY OF THE INVENTION

The invention is therefore concerned with a process for the manufacture of lycopene and intermediary phosphonium salts, which process comprises reacting 3,7,11-trimethyldodeca-1,4,6,10-tetraen-3-ol of the formula

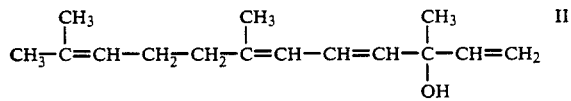

with a triarylphosphine and with a $C_1$–$C_6$-alkanoic acid or a boron trifluoride etherate to give the phosphonium salt of the general formula

wherein R signifies aryl and $Y^-$ signifies $C_1$–$C_6$-alkanoate or hydroxytrifluoroborate, if desired converting the phosphonium salt of formula I into the phosphonium salt of a strong acid and, if desired, reacting the phosphonium salt obtained with 2,7-dimethyl-2,4,6-octatrienedial to give lycopene.

The invention is also concerned with the novel phosphonium salts of formula I.

DETAILED DESCRIPTION

The term "aryl" above denotes usual aryl residues which are present in phosphines and phosphonium salts, such as phenyl, tolyl, naphthyl and the like, especially phenyl.

The term "$C_1$–$C_6$-alkanoate" denotes the anion of straight-chain or branched $C_1$–$C_6$-alkanoic acids such as formic acid, acetic acid, propionic acid, butyric acid, isobutyric acid, valeric acid, isovaleric acid and the like. The acetate and formate are preferred alkanoates. Accordingly, formic acid and acetic acid are preferred alkanoic acids.

The term "hydroxytrifluoroborate" denotes the anion $B(OH)F_3^-$.

The term "boron trifluoride etherate" embraces usual etherates of boron trifluoride, especially the etherates of straight-chain, branched or cyclic ethers having up to 8 carbon atoms such as dimethyl ether, diethyl ether, diisopropyl ether, t-butyl methyl ether, di-t-butyl ether, tetrahydrofuran and the like. Boron trifluoride diethyl etherate is especially preferred.

The term "strong acid" embraces hydrohalic acids (especially hydrochloric acid and hydrobromic acid), sulphuric acid, sulphonic acids (such as benzenesulphonic acid and toluenesulphonic acid), phosphoric acid and other inorganic or organic acids having a comparable degree of dissociation. The term "phosphonium salt of a strong acid" therefore denotes the phosphonium halides (especially the chlorides and bromides), sulphates, hydrogen sulphates, sulphonates, phosphates and the like.

The term "halogen" denotes in the scope of the present invention fluorine, chlorine, bromine and iodine, especially chlorine and bromine.

Formula I above embraces pure isomers and mixtures of isomers. Preferably, however, the 3,7,11-trimethyldodeca-2,4,6,10-tetraen-1-yl residue, which is depicted in formula I and which is referred to in the literature also as the Ψ-ionylidene-ethyl residue or pseudoionylidene-ethyl residue, is present in the all-E form. The phosphonium salts of formula I and the phosphonium salts of a strong acid which are obtainable therefrom are accordingly preferably 3,7,11-trimethyldodeca-2E,4E,6E,10-tetraen-1-yl-phosphonium salts (referred to hereinafter as the "all-E isomer"). Other preferred isomers are the 3,7,11-trimethyldodeca-2Z,4E,6E,10-tetraen-1-yl-phosphonium salts (referred to hereinafter as the "2Z isomer") and the 3,7,11-trimethyldodeca-2E,4E,6Z,10-tetraen-1-yl-phosphonium salts (referred to hereinafter as the "6Z isomer").

The 3,7,11-trimethyldodeca-1,4,6,10-tetraen-3-ol (also referred to as vinyl-Ψ-ionol or vinylpseudoionol) which is used as the educt in the reaction in accordance with the invention is known e.g. from Acta Chemica Scandinavica B29, 1015 (1975) and J. Chem. Soc. 1965, 2019 and can be obtained from pseudoionone according to known methods, e.g. by reaction with a vinyl-Grignard reagent or by reaction with lithium and acetylene and subsequent partial hydrogenation of the triple bond in the presence of a Lindlar catalyst. 3,7,11-Trimethyldodeca-1,4,6,10-tetraen-3-ol can be used as a mixture of isomers or as a pure isomer. Mixtures of isomers can be separated, if desired, by fractional distillation.

The reaction of 3,7,11-trimethyldodeca-1,4,6,10-tetraen-3-ol with a triarylphosphine and with a $C_1$–$C_6$-alkanoic acid or a boron trifluoride etherate can be effected in a manner known per se. The triarylphosphine is preferably used in at least about equimolar amounts, for example about 1-3 equivalents. In general, it is especially preferred to use a small excess of triarylphosphine, e.g. about 1.1-2 equivalents. Triphenylphosphine is the preferred triarylphosphine. The alkanoic acid and, respectively, the boron trifluoride etherate are conveniently used in at least about equimolar amounts. As a rule, a clear excess is preferred. Therefore, there are in general preferably used at least about 3 equivalents, particularly at least about 8 equivalents, of alkanoic acid and, respectively, boron trifluoride etherate. Formic acid and acetic acid are the preferred alkanoic acids and boron trifluoride diethyl etherate is the preferred boron trifluoride etherate. The reaction is conveniently effected in a solvent, whereby, however, the alkanoic acid or the ether corresponding to the etherate which is used can itself serve as the solvent and/or an inert organic solvent can be added to the mixture. Preferred inert organic solvents are optionally chlorinated or aromatic hydrocarbons, ethers, alcohols and esters such as hexane, methylene chloride, chloroform, benzene, toluene, xylene, diisopropyl ether, t-butyl methyl ether, tetrahydrofuran, methanol, ethanol, ethyl acetate and the like.

A preferred embodiment of the process in accordance with the invention comprises carrying out the reaction using formic acid in the presence of an inert organic solvent (especially in the presence of an optionally chlorinated or aromatic hydrocarbon). A further preferred embodiment comprises carrying out the reaction using acetic acid (or generally using a $C_2$-$C_6$-alkanoic acid) with or without the addition of an inert organic solvent (for example an optionally chlorinated or aromatic hydrocarbon). A third preferred embodiment comprises carrying out the reaction using a boron trifluoride etherate in the presence of an inert organic solvent (preferably an optionally chlorinated or aromatic hydrocarbon or an ether).

Temperature and pressure are not critical in the reaction of 3,7,11-trimethyldodeca-1,4,6,10-tetraen-3-ol. In general, the reaction is carried out at about 0°-100° C. and under normal pressure. A temperature range of about 40°-80° C., especially about 50°-65° C., is preferred.

The phosphonium salt of formula I which is obtained can be isolated from the reaction mixture if desired. As these phosphonium salts are, however, less stable in isolated form, they are preferably without previous isolation converted directly into lycopene or converted into more stable phosphonium salts by anion exchange.

The anion exchange, i.e. the conversion of the phosphonium salts of formula I into corresponding phosphonium salts of a strong acid, can be effected by reaction with a strong acid or with a soluble salt of the strong acid. The reaction can be carried out preferably using an aqueous solution of the strong acid or of the salt of the strong acid. It can preferably be effected during the working-up of the reaction mixture containing the phosphonium salt of formula I, for example by washing with the aqueous solution of the acid or of the salt. The alkali metal salts, especially the sodium salts and the potassium salts, are the preferred soluble salts of the strong acids. Hydrochloric acid, hydrobromic acid, sulphuric acid, phosphoric acid and sulphonic acids such as benzenesulphonic acid and toluenesulphonic acid are preferred strong acids. The alkali metal salts of these acids such as sodium chloride, potassium chloride, sodium bromide, sodium sulphate, sodium hydrogen sulphate, sodium phosphate, sodium tosylate and the like are especially preferred salts. The conversion into the chloride is especially preferred; it can be effected preferably using aqueous hydrochloric acid or using an aqueous solution of an alkali metal chloride (e.g. sodium chloride).

The conversion into the phosphonium salt of a strong acid by anion exchange is preferred as a rule when a purification or separation of isomers is effected prior to the Wittig reaction. Alternatively, the phosphonium salt of formula I can preferably be converted directly into lycopene.

The reaction of the phosphonium salts of formula I or of the corresponding phosphonium salts of strong acids with 2,7-dimethyl-2,4,6-octatrienedial can be carried out in a manner known per se and under conditions which are usual for Wittig reactions. Suitable conditions are well-known to the person skilled in the art. Examples of preferred methods are the reaction in methylene chloride/methanol in the presence of sodium methylate, in toluene/methanol in the presence of sodium methylate, in ethanol in the presence of sodium ethylate or in methylene chloride/water in the presence of potassium hydroxide or potassium carbonate. The reaction is preferably effected at about 0°-50° C. 2,7-Dimethyl-2E,4E,6E-octatrienedial is preferably used for the manufacture of all-trans-lycopene. The double bonds which newly result in the Wittig reaction are formed partially in the cis form. They can, however, be isomerized to the trans form according to usual methods (e.g. thermally). The isomerization often takes place even under the reaction conditions.

In the conversion of 3,7,11-trimethyldodeca-1,4,6,10-tetraen-3-ol into the phosphonium salt of formula I the configuration of the double bond in position 6 of 3,7,11-trimethyldodeca-1,4,6,10-tetraen-3-ol is largely retained. The double bond in position 4 of formula I is as a rule obtained in the E form independently of the configuration in the educt. The double bond in position 2 of formula I is mainly formed predominantly in the E form with a small amount of Z form. In order to avoid isomerization reactions as far as possible, 3,7,11-trimethyldodeca-1,4E,6E,10-tetraen-3-ol or a mixture of isomers having a high content of this isomer is therefore preferably used for the manufacture of all-E-lycopene. 3,7,11-Trimethyldodeca-1,4Z,6E,10-tetraen-3-ol is, however, equally well suited.

The present invention is illustrated in more detail by the following Examples. The yield of phosphonium salts and the isomer ratios were determined by high-pressure liquid chromatography (HPLC) with an internal standard for reasons of stability. The structures given were confirmed by nuclear magnetic resonance spectroscopy.

EXAMPLE 1

A mixture of 52.46 g of triphenylphosphine and 525 ml of glacial acetic acid was heated to 55° C. and then treated dropwise within 10 minutes with a mixture of 25.81 g of 3,7,11-trimethyldodeca-1,4E,6E,10-tetraen-3-ol (purity 85.3%) and 15 ml of hexane. Thereby, the temperature rose to 60° C. The mixture was stirred at 60° C. for a further 2.5 hours and then cooled to 25° C.

Subsequently, the reaction mixture containing 3,7,11-trimethyldodeca-2,4,6,10-tetraen-1-yl-triphenylphosphonium acetate [Rf value 0.41 (butyl acetate/formic acid/water 88:10:2)] was rinsed with 500 ml of methylene chloride into a separating funnel and, for the conversion into the chloride, washed six times with 500 ml of 2 percent sodium chloride solution each time. The organic phase was concentrated on a rotary evaporator. The residue was taken up in 200 ml of hexane and 300 ml of methanol/water (vol. 80:20). The hexane phase was separated and the methanol/water phase was extracted four times with 200 ml of hexane each time. The combined hexane phases were back-extracted twice with 20 ml of methanol/water (vol. 80:20) each time. The methanol/water phases were freed from methanol on a rotary evaporator at 40° C. The aqueous solution was rinsed with 200 ml of methylene chloride into a separating funnel and washed three times with 200 ml of 10 percent sodium chloride solution each time. The organic phase was concentrated on a rotary evaporator. In order to remove the methylene chloride completely, the residue was treated twice with ethyl acetate and concentrated each time. The crystalline crude product was taken up in ethyl acetate (a total of 420 g of mixture) and brought into solution by adding 4.47 ml of methanol and heating to 40° C. The solution was left to stand at room temperature overnight and was then filtered. The filter cake was washed with ethyl acetate.

The mother liquor containing the desired product was analyzed by HPLC with an internal standard. The analysis gave 36.67 g (73.2%) of 3,7,11-trimethyl-dodeca-2,4,6,10-tetraen-1-yl-triphenylphosphonium chloride consisting of 28.78 g (57.5%) of all-E isomer, 5.62 g (11.2%) of 2Z isomer and 2.27 g (4.5%) of 6Z isomer. Rf value 0.41 (butyl acetate/formic acid/water 88:10:2). The filter cake, which contained a further 7.19 g (14.3%) of product consisting of 2.13 g (4.2%) of all-E isomer, 1.48 g (3.0%) of 2Z isomer and 3.58 g (7.1%) of 6Z isomer, was not worked-up.

Analogous experiments (without crystallization) at 40° C., 60° C. and 80° C. yielded the following results in accordance with HPLC analysis:

| Temperature | Reaction time | Chemical yield | Amount of 6Z isomer |
| --- | --- | --- | --- |
| 40° C. | 6.5 h | 70% | 8.6% |
| 60° C. | 2.5 h | 96% | 10.9% |
| 80° C. | 1.5 h | 96% | 11.7% |

EXAMPLE 2

A mixture of 2.45 g of triphenylphosphine, 25 ml of methylene chloride and 4 ml of glacial acetic acid was heated to 40° C. and treated dropwise under argon within 10 minutes with 1.53 g of 3,7,11-trimethyl-dodeca-1,4E,6Z,10-tetraen-3-ol (purity 76.6%). The reaction mixture was stirred at 40° C. overnight and then concentrated on a rotary evaporator. The residue was transferred with 50 ml of methanol/water (vol. 80:20) into a separating funnel and extracted four times with 30 ml of hexane each time. The combined hexane phases were backwashed with 30 ml of methanol/water (vol. 80:20). The combined methanol phase containing the desired product was analyzed by HPLC with an internal standard. It contained 0.029 g (2.5%) of unreacted 3,7,11-trimethyldodeca-1,4,6,10-tetraen-3-ol and 2.26 g (81.3%) of 3,7,11-trimethyldodeca-2,4,6,10-tetraen-1-yl-triphenylphosphonium acetate consisting of 1.36 g (48.9%) of 6Z isomer, 0.64 g (23.0%) of all-E isomer and 0.26 g (9.4%) of 2Z isomer. Rf value 0.41 (butyl acetate/formic acid/water 88:10:2).

EXAMPLE 3

A mixture of 2.45 g of triphenylphosphine, 25 ml of hexane and 4 ml of glacial acetic acid was heated to 45° C. and treated dropwise under argon within 10 minutes with 1.53 g of 3,7,11-trimethyldodeca-1,4E,6Z,10-tetraen-3-ol (purity 76.6%). The reaction mixture was stirred at 45° C. overnight and then concentrated on a rotary evaporator. The residue was transferred with 50 ml of methanol/water (vol. 80:20) into a separating funnel and extracted four times with 30 ml of hexane each time. The combined hexane phases were back-washed with 30 ml of methanol/water (vol. 80:20). The combined methanol phase containing the desired product was analyzed by HPLC with an internal standard. It contained 0.03 g (3%) of unreacted 3,7,11-trimethyl-dodeca-1,4,6,10-tetraen-3-ol and 2.14 g (77.0%) of 3,7,11-trimethyldodeca-2,4,6,10-tetraen-1-yl-triphenylphosphonium acetate consisting of 1.22 g (43.9%) of 6Z isomer, 0.67 g (24.1%) of all-E isomer and 0.25 g (9.0%) of 2Z isomer. Rf value 0.41 (butyl acetate/formic acid/water 88:10:2).

EXAMPLE 4

A mixture of 7.85 g of triphenylphosphine, 78.5 ml of hexane and 9.5 ml of formic acid was treated dropwise while stirring and gassing with nitrogen at 60° C. within 10 minutes with a solution of 8.3 g of 3,7,11-trimethyl-dodeca-1,4E,6E,10-tetraen-3-ol (purity 66.5%) in 8 ml of hexane. The reaction mixture was stirred at 60° C. for a further 2.5 hours and then rinsed with 125 ml of methanol/water (vol. 80:20) into a separating funnel. The hexane phase was separated and the methanol phase was washed three times with 125 ml of hexane each time. The hexane phases were back-extracted twice with 25 ml of methanol/water (vol. 80:20) each time. The methanol phases containing 3,7,11-trimethyl-dodeca-2,4,6,10-tetraen-1-yl-triphenylphosphonium formate [Rf value 0.41 (butyl acetate/formic acid/water 88:10:2)] were combined and evaporated.

The residue was taken up in 200 ml of methylene chloride and, for the conversion into the chloride, washed five times with 250 ml of 2 percent sodium chloride solution each time. The organic phase was evaporated and the residue was taken up in methanol and analyzed by HPLC with an internal standard. The product solution contained 12.31 g (96.3%) of 3,7,11-trimethyldodeca-2,4,6,10-tetraen-1-yl-triphenylphosphonium chloride consisting of 7.97 g (62.3%) of all-E isomer, 2.8 g (21.9%) of 6Z isomer and 1.54 g (12.1%) of 2Z isomer. Rf value 0.41 (butyl acetate/formic acid/water 88:10:2).

EXAMPLE 5

A mixture of 3.2 g of triphenylphosphine, 11.9 ml of methylene chloride and 1.53 ml of formic acid was treated dropwise at 30° C. within 60 minutes with 1.35 g of 3,7,11-trimethyldodeca-1,4E,6E,10-tetraen-3-ol (purity 66.3%). The mixture was stirred at 30° C. for a further 17 hours.

Subsequently, the reaction mixture containing 3,7,11-trimethyldodeca-2,4,6,10-tetraen-1-yl-triphenylphosphonium formate [Rf value 0.41 (butyl acetate/formic acid/water 88:10:2)] was rinsed with 50 ml of methylene chloride into a separating funnel and, for the conversion into the chloride, washed twice with 125 ml of 2 percent sodium chloride solution each time. The organic phase was concentrated on a rotary evaporator and the residue was taken up in methanol and analyzed by HPLC with an internal standard. The product solution contained 1.69 g (81.8%) of 3,7,11-trimethyldodeca-2,4,6,10-tetraen-1-yl-triphenylphosphonium chloride consisting of 1.14 g (55.1%) of all-E isomer, 0.32 g (15.6%) of ZZ isomer and 0.23 g (11.1%) of 6Z isomer. Rf value 0.41 (butyl acetate/formic acid/water 88:10:2).

EXAMPLE 6

A mixture of 2.27 g of triphenylphosphine, 22.5 ml of toluene and 0.85 ml of formic acid was treated dropwise at 55° C. within 5 minutes with 1.1 g of 3,7,11-trimethyl-dodeca-1,4E,6Z,10-tetraen-3-ol (purity about 75%). In so doing the temperature rose to 60° C. The mixture was stirred at 60° C. for a further 2.5 hours.

Subsequently, the reaction mixture containing 3,7,11-trimethyldodeca-2,4,6,10-tetraen-1-yl-triphenylphosphonium formate [Rf value 0.41 (butyl acetate/formic acid/water 88:10:2)] was rinsed with 50 ml of toluene into a separating funnel and, for the conversion into the chloride, washed twice with 125 ml of 2 percent sodium chloride solution each time. The organic phase was concentrated on a rotary evaporator and the residue was taken up in methanol and analyzed by HPLC with an internal standard. The product solution contained 1.618 g (84.2%) of 3,7,11-trimethyldodeca-2,4,6,10-tetraen-1-yl-triphenylphosphonium chloride consisting of 0.931 g (48.2%) of 6Z isomer, 0.480 g (25.2%) of all-E isomer and 0.207 g (10.8%) of 2Z isomer. Rf value 0.41 (butyl acetate/formic acid/water 88:10:2).

EXAMPLE 7

A mixture of 3.54 g of triphenylphosphine, 50 ml of t-butyl methyl ether and 3.32 g of 3,7,11-trimethyl-dodeca-1,4E,6E,10-tetraen-3-ol (purity 66.3%) was treated dropwise at 53° C. within 35 minutes with a solution of 1.30 ml of boron trifluoride diethyl etherate in 25 ml of t-butyl methyl ether. The mixture was stirred at 53° C. for a further 2.5 hours and then concentrated on a rotary evaporator. The residue was rinsed with 80 ml of methanol/water (vol. 80:20) into a separating funnel and extracted four times with 50 ml of hexane each time. The hexane phases were combined and back-washed twice with 10 ml of methanol/water (vol. 80:20) each time. The methanol phases containing 3,7,11-trimethyldodeca-2,4,6,10-tetraen-1-yl-triphenylphosphonium hydroxytrifluoroborate [Rf value 0.41 (butyl acetate/formic acid/water 88:10:2)] were concentrated on a rotary evaporator.

The residue was rinsed with 80 ml of methylene chloride into a separating funnel and, for the conversion into the chloride, washed three times with 125 ml of 2 percent sodium chloride solution each time. The organic phases were concentrated on a rotary evaporator and the residue was taken up in methanol and analyzed by HPLC with an internal standard. The product solution contained 3.404 g (61.9%) of 3,7,11-trimethyldodeca-2,4,6,10-tetraen-1-yl-triphenylphosphonium chloride consisting of 2.403 g (43.7%) of all-E isomer, 0.528 g (9.6%) of 2Z isomer and 0.473 g (8.6%) of 6Z isomer. Rf value 0.41 (butyl acetate/formic acid/water 88:10:2).

EXAMPLE 8

41.2 g of 3,7,11-trimethyldodeca-2,4,6,10-tetraen-1-yl-triphenylphosphonium chloride (prepared according to Example 1) and 5.4 g of 2,7-dimethyl-2E,4E,6E-octatrienedial were dissolved in 410 ml of methylene chloride. The solution was cooled to −5° C. and treated dropwise within 15 minutes with 25.1 g of sodium methylate solution (containing 4.7 g of sodium methylate in 20.4 g of methanol). The reaction mixture was stirred at −5° C. for 30 minutes, then warmed to 20° C. within 10 minutes and stirred at 20° C. for a further 60 minutes. Subsequently, the reaction mixture was transferred into a separating funnel and washed twice with 300 ml of 1 percent sodium chloride solution each time. The organic phase was concentrated to a volume of 100 ml on a rotary evaporator. Subsequently, the methylene chloride was evaporated under normal pressure and replaced by methanol. The mixture was left to cool and was stored at 5° C. overnight in order to complete the crystallization. The crystallizate was filtered off under suction and washed with 50 ml of methanol. There were thus obtained 18.2 g of lycopene in a purity of 86.1% (according to HPLC with an internal standard). The yield was 89.0% based on 2,7-dimethyl-2E,4E,6E-octatrienedial. The mother liquor, which contained a further 2% of lycopene, was not worked-up.

EXAMPLE 9

A mixture of 5.25 g of triphenylphosphine and 52.5 ml of glacial acetic acid was heated to 55° C. and then treated dropwise within 10 minutes with 2.34 g of 3,7,11-trimethyldodeca-1,4E,6E,10-tetraen-3-ol (purity 84.4%). The reaction mixture was stirred at 60° C. for a further 2.5 hours, then cooled to room temperature and concentrated on a rotary evaporator to a large extent. The residue, which still contained some glacial acetic acid, was rinsed with 100 ml of hexane and 100 ml of methanol/water (vol. 80:20) into a separating funnel and extracted three times with 100 ml of hexane each time. The combined hexane phases were back-washed twice with 10 ml of methanol/water (vol. 80:20) each time and then concentrated on a rotary evaporator. The residue was taken up immediately in 100 ml of methylene chloride. The methylene chloride phase was washed with water and concentrated on a rotary evaporator. There were thus obtained 4.0 g of a crude product of 3,7,11-trimethyldodeca-2,4,6,10-tetraen-1-yl-triphenylphosphonium acetate which was further reacted immediately.

The phosphonium acetate obtained and 0.5 g of 2,7-dimethyl-2E,4E,6E-octatrienedial were dissolved in 40 ml of methylene chloride. The solution was cooled to −10° C. and treated dropwise within 5 minutes with 2.4 g of sodium methylate solution (containing 0.44 g of sodium methylate in 1.96 g of methanol). The reaction mixture was stirred at −10° C. for 2.5 hours, then warmed to room temperature and treated with 70 ml of water. Subsequently, the reaction mixture was transferred with methylene chloride into a separating funnel and the aqueous phase was separated. The lycopene obtained was detected by thin-layer chromatography; Rf value 0.92 (methylene chloride/diethyl ether 99:1).

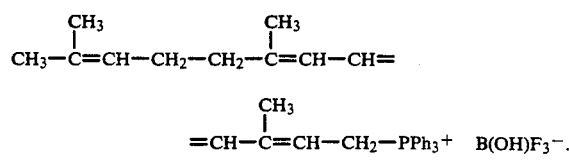

I claim:
1. A compound of the formula